United States Patent
Yu et al.

(10) Patent No.: US 8,337,809 B2
(45) Date of Patent: Dec. 25, 2012

(54) CHARGE-ASSEMBLED CAPSULES FOR PHOTOTHERAPY

(75) Inventors: Jie Yu, Houston, TX (US); Michael Sha-nang Wong, Houston, TX (US); Bahman Anvari, Tustin, CA (US); Mohammad Abbas Yaseen, Somerville, MA (US)

(73) Assignee: William Marsh Rice University, Houston, TX (US)

( * ) Notice: Subject to any disclaimer, the term of this patent is extended or adjusted under 35 U.S.C. 154(b) by 531 days.

(21) Appl. No.: 12/440,715

(22) PCT Filed: Sep. 11, 2007

(86) PCT No.: PCT/US2007/078150
§ 371 (c)(1),
(2), (4) Date: Oct. 29, 2009

(87) PCT Pub. No.: WO2008/088586
PCT Pub. Date: Jul. 24, 2008

(65) Prior Publication Data
US 2010/0047356 A1    Feb. 25, 2010

Related U.S. Application Data

(60) Provisional application No. 60/825,257, filed on Sep. 11, 2006.

(51) Int. Cl.
*A61K 51/00* (2006.01)
*A61K 51/12* (2006.01)
(52) U.S. Cl. ...................................................... 424/1.29
(58) Field of Classification Search ........................ None
See application file for complete search history.

(56) References Cited

U.S. PATENT DOCUMENTS 4,692,462 A    9/1987  Banerjee
7,230,088 B2 *  6/2007  Rajagopalan et al. ........ 530/405
(Continued)

FOREIGN PATENT DOCUMENTS

WO    2004064751 A2    8/2004
(Continued)

OTHER PUBLICATIONS

Yaseen, Mohammad A., et al., "Laser-induced heating of dextran-coated mesocapsules containing indocyanine green," Biotechnol. Prog., 2007, pp. 1431-1440, vol. 23, No. 6, American Chemical Society and American Institute of Chemical Engineers.

(Continued)

*Primary Examiner* — Anand Desai
*Assistant Examiner* — Melissa Mercier
(74) *Attorney, Agent, or Firm* — Conley Rose, P.C.; Rodney B. Carroll (57) ABSTRACT

Novel phototherapeutic methods and compositions are described herein. Nanoparticle-assembled microcapsules as a new type of delivery vehicle for photosensitive compounds may be synthesized through a two-step assembly process. Charged polymer chains and counterions may be combined with a photosensitive compound to form photosensitive aggregates, and then nanoparticles may be combined with the aggregates to form the microcapsules. The shell may be composed of nanoparticles and/or polymer, and the core interior may contain the photosensitive compound. Formation occurs rapidly (on the order of seconds) and the conditions are very mild (at room temperature, in aqueous solution, and at neutral pH). The microcapsule synthesis is highly suitable as an encapsulation method, particularly for a charged photosensitive molecule like ICG.

7 Claims, 9 Drawing Sheets

U.S. PATENT DOCUMENTS

| | | | |
|---|---|---|---|
| 8,007,829 B2* | 8/2011 | Murthy et al. | 424/489 |
| 2004/0013721 A1 | 1/2004 | Antipov et al. | |
| 2004/0156783 A1* | 8/2004 | Rajagopalan et al. | 424/9.6 |
| 2005/0158390 A1 | 7/2005 | Rana et al. | |
| 2005/0202096 A1 | 9/2005 | Li et al. | |
| 2006/0159921 A1* | 7/2006 | Murthy et al. | 428/402 |

FOREIGN PATENT DOCUMENTS

| | | |
|---|---|---|
| WO | 2008088586 A2 | 7/2008 |
| WO | 2008088586 A3 | 7/2008 |
| WO | 2008088586 A9 | 7/2008 |

OTHER PUBLICATIONS

Yu, Jie, et al., "Synthesis of nanoparticle-assembled tin oxide/polymer microcapsules," Chem, Commun., 2006, pp. 1097-1099, The Royal Society of Chemistry.

Yu, Jie, et al., "Synthesis of near-infrared-absorbing nanoparticle-assembled capsules," Chem. Mater., 2007, pp. 1277-1284, vol. 19, No. 6, American Chemical Society.

Yuan, Baohong, et al., "Emission and absorption properties of indocyanine green in intralipid solution," Journal of Biomedical Optics, May/Jun. 2004, pp. 497-503, vol. 9, No. 3, SPIE.

Zhou, Jin Fu, et al., "Aggregation and degradation of indocyanine green," 1994, pp. 495-505, vol. 2128, SPIE.

Abels, C., et al., "Indocyanine green and laser light for the treatment of AIDS-associated cutaneous Kaposi's sarcoma," British Journal of Cancer, 1998, pp. 1021-1024, vol. 77, No. 6, Cancer Research Campaign.

Angelatos, Alexandra S., et al., "Light-responsive polyelectrolyte/gold nanoparticle microcapsules," J. Phys. Chem. B, 2005, pp. 3071-3076, vol. 109, No. 7, American Chemical Society.

Barbier, F., et al., "Chromatography and I.R. spectrography of indocyanine green," 1964, pp. 549-554, vol. 10, Clinica Chimica Acta.

Bashkatov, A. N., et al., "Optical properties of human skin, subcutaneous and mucous tissues in the wavelength range from 400 to 2000 nm," Journal of Physics D: Applied Physics, 2005, pp. 2543-2555, vol. 38, Institute of Physics Publishing, IOP Publishing Ltd, United Kingdom.

Bäumler, W., et al., "Photo-oxidative killing of human colonic cancer cells using indocyanine green and infrared light," British Journal of Cancer, 1999, pp. 360-363, vol. 80, No. 3/4, Cancer Research Campaign.

Benson, R. C., et al., "Fluorescence properties of indocyanine green as related to angiography," 1978, pp. 159-163, vol. 23, No. 1, Phys. Med. Biol.

Brunner, Tobias J., "In vitro cytotoxicity of oxide nanoparticles: comparison to asbestos, silica, and the effect of particle solubility," Environmental Science & Technology, 2006, pp. 4374-4381, vol. 40, No. 14, American Chemical Society.

Chen, Wei R., et al., "Chromophore-enhanced in vivo tumor cell destruction using an 808-nm diode laser," Cancer Letters, 1995, pp. 125-131, vol. 94, Elsevier Science Ireland Ltd.

Chen, Wei R., et al., "Photothermal effects on murine mammary tumors using indocyanine green and an 808-nm diode laser: an in vivo efficacy study," Cancer Letters, 1996, pp. 169-173, vol. 98, Elsevier Science Ireland Ltd.

Desmettre, T., et al., "Fluorescence properties and metabolic features of indocyanine green (ICG) as related to angiography," Survey of Ophthalmology, Jul.-Aug. 2000, pp. 15-27, vol. 45, No. 1, Elsevier Science Inc.

Devoisselle, J. M., et al., "A preliminary study of the in vivo behaviour of an emulsion formulation of indocyanine green," Lasers Med Sci, 1998, pp. 279-282, vol. 13, Springer-Verlag London Limited.

Dorshow, Richard B., et al., "Noninvasive fluorescence detection of hepatic and renal function," Journal of Biomedical Optics, Jul. 1998, pp. 340-345, vol. 3, No. 3, Society of Photo-Optical Instrumentation Engineers.

Elias, Z., et al., "Cytotoxic and transforming effects of silica particles with different surface properties in Syrian hamster embryo (SHE) cells," Toxicology in Vitro, 2000, pp. 409-422, vol. 14, Elsevier Science Ltd.

Environmental Protection Agency (EPA), "Silica, amorphous, fumed (crystalline free); exemption from the requirement of a tolerance," Federal Register [Rules and Regulations], May 15, 2002, pp. 1-11, vol. 67, No. 94, http://www.epa.gov/EPA-PEST/2002/May/Day-15/p11743.htm.

Foreign communication from a related counterpart application—International Preliminary Report on Patentability, PCT/US2007/078150, Mar. 17, 2009, 6 pages.

Foreign communication from a related counterpart application—International Search Report and Written Opinion, PCT/US07/78150, Jul. 18, 2008, 7 pages.

Gathje, Joan, et al., "Stability studies on indocyanine green dye," Aug. 1970, pp. 181-185, vol. 29, No. 2, Journal of Applied Physiology.

Genina, Elina A., et al., "Low-intensity indocyanine-green laser phototherapy of acne vulgaris: pilot study," Journal of Biomedical Optics, Jul./Aug. 2004, pp. 828-834, vol. 9, No. 4, SPIE.

Gratz, H., et al., "Photo-isomerisation, triplet formation, and photo-degradation dynamics of indocyanine green solutions," Journal of Photochemistry and Photobiology A: Chemistry, 1999, pp. 101-109, vol. 128, Elsevier Science S.A.

Hawrysz, Daniel J., et al., "Developments toward diagnostic breast cancer imaging using near-infrared optical measurements and fluorescent contrast agents," Neoplasia, Sep.-Oct. 2000, pp. 388-417, vol. 2, No. 5, Nature America, Inc.

Hollins, Bettye, et al., "Fluorometric determination of indocyanine green in plasma," 1987, pp. 765-768, vol. 33, No. 6, Clinical Chemistry.

Holzer, W., et al., "Photostability and thermal stability of indocyanine green," Journal of Photochemistry and Photobiology B: Biology, 1998, pp. 155-164, vol. 47, Elsevier Science S.A.

Hunter, Robert J., "Foundations of colloid science," Second Edition, 2001, 2 pages, published in the United States by Oxford University Press Inc., New York, © Robert J. Hunter.

Intes, Xavier, et al., "In vivo continuous-wave optical breast imaging enhanced with indocyanine green," Medical Physics, Jun. 2003, pp. 1039-1047, vol. 30, No. 6, Am. Assoc. Phys. Med.

Kim, Dong-Eog, et al., "Near-infrared fluorescent imaging of cerebral thrombi and blood-brain barrier disruption in a mouse model of cerebral venous sinus thrombosis," Journal of Cerebral Blood Flow & Metabolism, 2005, pp. 226-233, vol. 25, ISCBFM.

Landsman, M. L. J., et al., "Light-absorbing properties, stability, and spectral stabilization of indocyanine green," Apr. 1976, pp. 575-583, vol. 40, No. 4, Journal of Applied Physiology.

Lund-Johansen, P., et al., "Effect of long-term diltiazem treatment on central haemodynamics and exercise endurance in essential hypertension," European Heart Journal, 1990, pp. 543-551, vol. 11, The European Society of Cardiology.

Maarek, Jean-Michel I., et al., "Measurement of cardiac output with indocyanine green transcutaneous fluorescence dilution technique," Anesthesiology, Jun. 2004, pp. 1476-1483, vol. 100, No. 6, American Society of Anesthesiologists, Inc. Lippincott Williams & Wilkins, Inc.

Maarek, Jean-Michel L, et al., "Transcutaneous fluorescence dilution cadiac output and circulating blood volume during hemorrhagic hypovolemia," Anesthesiology, Apr. 2005, pp. 774-782, vol. 102, No. 4, American Society of Anesthesiologists, Inc. Lippincott Williams & Wilkins, Inc.

Milstein, Adam B., et al., "Fluorescence optical diffusion tomography," Applied Optics, Jun. 1, 2003, pp. 3081-3094, vol. 42, No. 16, Optical Society of America.

Mordon, S., et al., "Laser-induced release of liposome-encapsulated dye: a new diagnostic tool," Lasers Med Sci, 1998, pp. 181-188, vol. 13, Springer-Verlag London Limited.

Mordon, Serge, et al., "Indocyanine green: physicochemical factors affecting its fluorescence in vivo," Microvascular Research, 1998, pp. 146-152, vol. 55, Academic Press.

Murthy, Vinit S., et al., "Nanoparticle-assembled capsule synthesis: formation of colloidal polyamine—salt intermediates," J. Phys. Chem. B, 2006, pp. 25619-25627, vol. 110, No. 51, American Chemical Society.

Patonay, Gabor, et al., "Noncovalent labeling of biomolecules with red and near-infrared dyes," http://www.mdpi.org, 2004, pp. 40-49, vol. 9, Molecules.

Provisional patent application entitled "Phototherapeutic materials prepared through nanoparticle assembly," by Jie Yu, et al., filed Sep. 11, 2006 as U.S. Appl. No. 60/825,257.

Rana, Rohit K., et al., "Nanoparticle self-assembly of hierarchically ordered microcapsule structures," Advanced Materials, 2005, pp. 1145-1150, vol. 17, WILEY-VCH Verlag GmbH & Co. KGaA, Weinheim.

Saxena, Vishal, et al., "Degradation kinetics of indocyanine green in aqueous solution," Journal of Pharmaceutical Sciences, Oct. 2003, pp. 2090-2097, vol. 92, No. 10, Wiley-Liss, Inc. and the American Pharmacists Association.

Saxena, Vishal, et al., "Indocyanine green-loaded biodegradable nanoparticles: preparation, physicochemical characterization and in vitro release," International Journal of Pharmaceutics, 2004, pp. 293-301, vol. 278, Elsevier B.V.

Saxena, Vishal, et al., "Polymeric nanoparticulate delivery system for indocyanine green: biodistribution in healthy mice," International Journal of Pharmaceutics, 2006, pp. 200-204, vol. 308, Elsevier B.V.

Saxena, Vishal, et al., "Enhanced photo-stability, thermal-stability and aqueous-stability of indocyanine green in polymeric nanoparticulate systems," Journal of Photochemistry and Photobiology B: Biology, 2004, pp. 29-38, vol. 74, Elsevier B.V.

Skirtach, Andre G., et al., "Remote activation of capsules containing Ag nanoparticles and IR dye by laser light," Langmuir, 2004, pp. 6988-6992, vol. 20, No. 17, American Chemical Society.

Skirtach, Andre G., et al., "The role of metal nanoparticles in remote release of encapsulated materials," Nano Letters, 2005, pp. 1371-1377, vol. 5, No. 7, American Chemical Society.

Skirtach, Andre G., et al., "Laser-induced release of encapsulated materials inside living cells," Angew. Chem. Int. Ed., 2006, pp. 4612-4617, vol. 45, Wiley-VCH Verlag GmbH & Co. KGaA, Weinheim.

Taichman, Gerald C., et al., "The use of cardio-green for intraoperative visualization of the coronary circulation: evaluation of myocardial toxicity," Jun. 1987, pp. 133-138, vol. 14, No. 2, Texas Heart Institute Journal.

Tuchin, Valery V., et al., "A pilot study of ICG laser therapy of acne vulgaris: photodynamic and photothermolysis treatment," Lasers in Surgery and Medicine, 2003, pp. 296-310, vol. 33, Wiley-Liss, Inc.

Urbanska, Krystyna, et al., "Indocyanine green as a prospective sensitizer for photodynamic therapy of melanomas," 2002, pp. 387-391, vol. 49, No. 2, Acta Biochimica Polonica.

Wolfe, Jeremy D., et al., "Indocyanine green enhanced retinal vessel laser closure in rats: histologic and immunohistochemical observations," Experimental Eye Research, 2004, pp. 631-638, vol. 79, Elsevier Ltd.

World Health Organization International Agency for Research on Cancer, "IARC monographs on the evaluation of carcinogenic risks to humans—silica, some silicates, coal dust and para-aramid fibrils," 1997, 1 cover page, 1 publishing page, and pp. 41 and 42, vol. 68, IARC, Lyon, France.

Yaseen, Mohammad A., et al., "Biodistribution of encapsulated indocyanine green in healthy mice," Molecular Pharmaceutics, 2009, pp. 1321-1332, vol. 6, No. 5, American Chemical Society.

Yaseen, Mohammad A., et al., "In-vivo fluorescence imaging of mammalian organs using charge-assembled mesocapsule constructs containing indocyanine green," Optics Express, Dec. 8, 2008, pp. 20577-20587, vol. 16, No. 25, Optical Society of America (OSA).

Yaseen, Mohammad A., et al., "Biodistribution of encapsulated Indocyanine Green in healthy mice," author manuscript, pp. 1-20 (published in final edited form as Mol Pharm., 2009, pp. 1321-1332, vol. 6, No. 5).

* cited by examiner

CHARGE-ASSEMBLED CAPSULES FOR PHOTOTHERAPY

CROSS-REFERENCE TO RELATED APPLICATIONS

This application is a filing under 35 U.S.C. §371 of International Application No. PCT/US2007/078150 filed Sep. 11, 2007 by Jie Yu, et al. and entitled "New Phototherapeutic Materials Prepared Through Nanoparticle Assembly," which claims priority to U.S. Provisional Patent Application Ser. No. 60/825,257 filed Sep. 11, 2006 by Jie Yu, et al. and entitled "New Phototherapeutic Materials Prepared Through Nanoparticle Assembly," both of which are incorporated herein by reference as if reproduced in their entirety.

STATEMENT REGARDING FEDERALLY SPONSORED RESEARCH OR DEVELOPMENT

This research was funded by a Smalley-Curl Innovation Award (MSW), 3M Nontenured Faculty Award (MSW), and with government support under Grant Numbers NIH GMO-8362 (MAY) and NIH R01-AR47996 (BA), awarded by the National Institutes of Health. The government has certain rights in the invention.

REFERENCE TO A MICROFICHE APPENDIX

Not applicable.

BACKGROUND

1. Field of the Invention

This invention relates generally to the field of nanoencapsulation. More specifically, the invention relates to a method of delivering phototherapeutic materials.

2. Background of the Invention

Photosensitive compounds such as indocyanine green (ICG) have been extensively studied as a basis for various medical treatments. These compounds can convert absorbed light energy to produce heat and chemical species, forming the bases for phototherapeutic (e.g. photothermal and photodynamic) treatments. Specific applications under investigation include laser tissue welding and treatment of skin diseases and cancers. There are several problems that limit the development of photosensitive compounds for new phototherapy applications. First, the pharmacokinetics of the photosensitive compound may be extremely fast. For example, ICG clears rapidly from the circulatory system with a half-life of 3-4 min, followed by a much slower clearance rate characterized by a half-life of 1+ hr. Second, certain photosensitive compounds have complicated solution behaviors due to their amphiphilic nature. They may have a tendency to aggregate in water depending on their concentration (bathochromically shifting absorbance characteristics of the compounds and reducing their fluorescence quantum efficiency) and may bind nonspecifically to human serum albumin, lipoproteins, plasma proteins, and endothelial cells. Some photosensitive compound solutions are unstable as the photosensitive compound undergoes thermal degradation and photodegradation.

The preparation of colloidal carriers for photosensitive compounds has been studied to address the issues of fast blood clearance and uncontrolled protein binding. Emulsions, like a phospholipid-stabilized oil-in-water system and a lecithin-stabilized commercial product called Intralipid, are one such material. It has been reported that blood clearance time may be lengthened but that the instability of the emulsion structure led to photosensitive compound leakage. Polymeric particles have recently been studied as another photosensitive compound carrier. Polymeric hollow spheres containing light-responsive dyes or nanoparticles may be prepared through a technique called layer-by-layer assembly. Among this technique's drawbacks are the numerous steps in their preparation and encapsulation, and capsule deformation upon drying due to their thin nm-scale shells.

Consequently, there is a need for simple methods and compositions for phototherapeutic treatments which prevent photosensitive compound leakage and also provide for repeated treatments.

BRIEF SUMMARY

New phototherapeutic methods and compositions are described herein. Nanoparticle-assembled microcapsules as a new type of delivery vehicle for photosensitive compounds may be synthesized through a two-step assembly process. The novel microcapsules may each comprise a photosensitive aggregate core surrounded by an outer shell. Charged polymer chains and counterions may be combined with a photosensitive compound to form the photosensitive aggregate cores, and then nanoparticles may be combined with the aggregate cores to form the outer shell of the microcapsules. The outer shell may be composed of nanoparticles and/or polymer, and the core interior may contain the photosensitive aggregate core. Formation occurs rapidly (on the order of seconds) and the conditions are very mild (at room temperature, in aqueous solution, and at neutral pH). The microcapsule synthesis is highly suitable as an encapsulation method, particularly for a charged photosensitive molecule like ICG. Further advantages and aspects of embodiments of the method are disclosed in more detail below.

In an embodiment, a phototherapeutic method comprises encapsulating one or more photosensitive compounds within a microcapsule to form a photosensitive microcapsule. The microcapsule comprises a polymer aggregate core surrounded by an outer shell. The method also comprises administering the one or more photosensitive microcapsules into a patient. In addition, the method comprises irradiating the one or more microcapsules with light so as provide phototherapeutic treatment to the patient.

In another embodiment, a method of encapsulating a photosensitive compound comprises providing an amount of a polyelectrolyte having a charge and an amount of a counterion having a valence of at least 2. Moreover, the method comprises combining the polyelectrolyte and the counterion in a solution such that the polyelectrolyte self-assembles to form one or more aggregate cores. The method additionally comprises adding the one or more photosensitive compounds to the aggregate cores to form one or more photosensitive aggregate cores. Further, the method comprises adding nanoparticles to the photosensitive aggregate cores such that nanoparticles arrange themselves around the photosensitive aggregates to form an outer shell and encapsulate the photosensitive compound.

In an embodiment, a photosensitive composition comprises a photosensitive compound and one or more microcapsules encapsulating said photosensitive compound. Each of the one or more microcapsules comprises a polymer aggregate core surrounded by a nanoparticle shell. The photosensitive compound is coupled to the polymer aggregate core.

A novel aspect of the disclosed methods and compositions are the ability to entrap and encapsulate water-soluble photosensitive compounds nondestructively and simply, to generate photosensitive capsule materials. The photosensitive capsules may be heated up multiple times using a light source, unlike unencapsulated photosensitive compounds. The enhanced stability and minimal leakage of the photosensitive compound are superior to other existing encapsulation materials.

The foregoing has outlined rather broadly the features and technical advantages of embodiments of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

(scale bar=10 μm); and

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ".

As used herein, the term "nanoparticle(s)" refers to particles having an average diameter ranging from about 1 nm to about 100 nm.

As used herein, the term "microcapsule" refers to a microparticle with an outer shell enclosing a hollow or liquid core. A microcapsule has an average diameter ranging from about 1 μm to about 1,000 μm.

As used herein, a patient refers to any human, mammal, and/or animal that may be treated using the disclosed therapies and compositions.

DETAILED DESCRIPTION OF THE PREFERRED EMBODIMENTS

Figure 1:
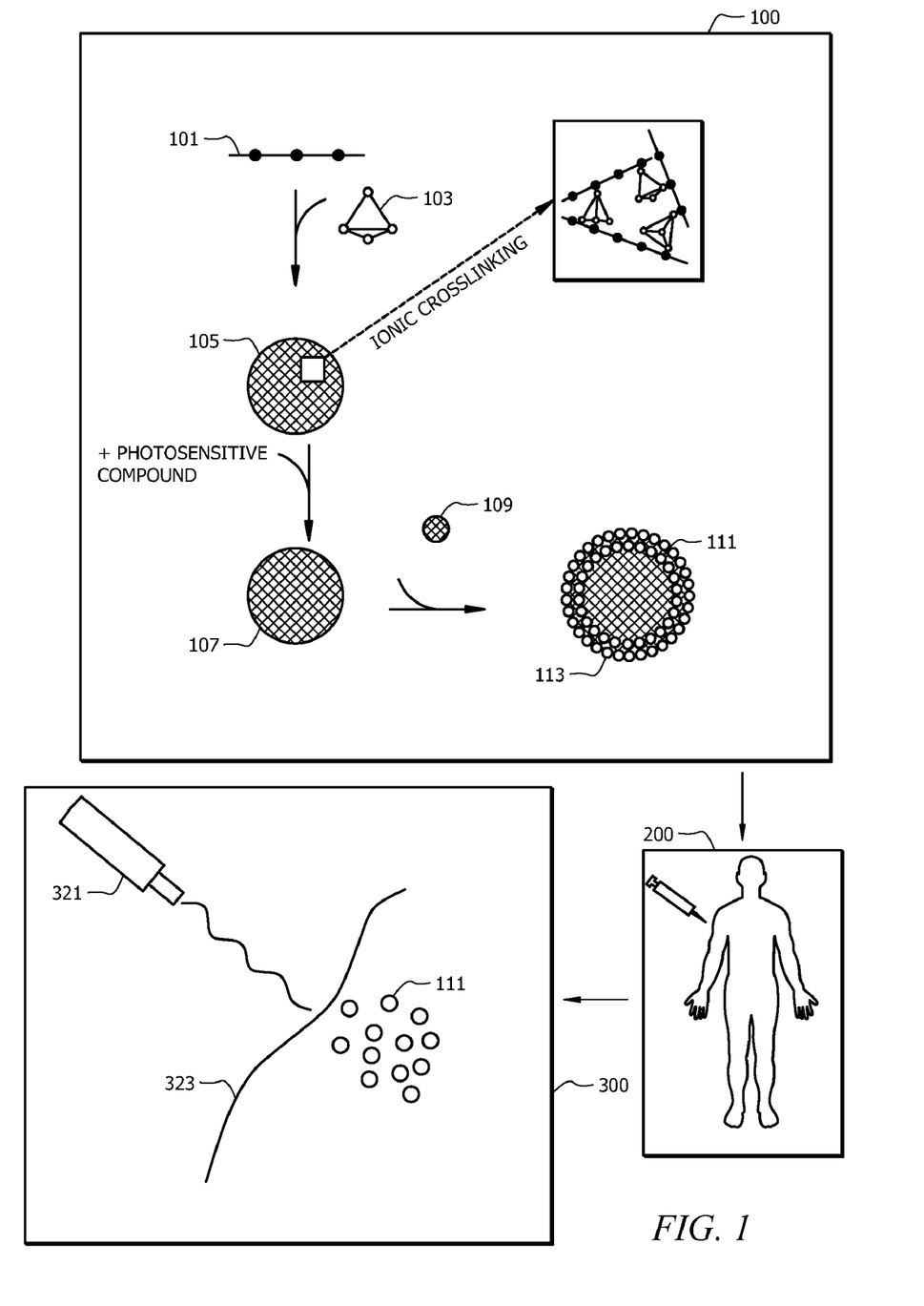
FIG. 1 illustrates an embodiment of a method of providing phototherapeutic treatment.

FIG. 1 illustrates an embodiment of a method for providing phototherapeutic treatment. The method generally comprises encapsulating a photosensitive compound in one or more microcapsules to form photosensitive microcapsules 113 at block 100. As used herein, the term "photosensitive" describes compositions or compounds that react when exposed to electromagnetic radiation (e.g. light). Specifically, the microcapsules are novel hybrid particles having a polymer aggregate core 107 and an outer shell 111. Encapsulating the photosensitive compound may prevent thermal and photo degradation of the photosensitive compound. That is, the microcapsule 113 may act as a protective barrier to improve the stability of the photosensitive compound contained therein. The photosensitive microcapsules 113 may then be administered to a patient either systemically or in situ (i.e. the site of treatment) at block 200. Functionalizing the photosensitive microcapsules may allow for targeted delivery after systemic administration. The microcapsules 113 are irradiated with a light source 321 (e.g. a laser) to excite the photosensitive compound and provide phototherapeutic treatment to the patient at block 300.

In an embodiment, the method comprises encapsulating a photosensitive compound in a microcapsule 113 as shown in FIG. 1. As mentioned above, the microcapsule 113 comprises a polymer aggregate core 105. In an exemplary embodiment, encapsulating the photosensitive compound may comprise adding counterions 103 to a solution of charged polyelectrolyte 101 so as to cause the polyelectrolyte 101 to self-assemble, along with the counterions 103, into aggregates 105. The selected counterion(s) 103 is/are added to a solution of the polyelectrolyte 101 in a concentration sufficient to produce a desired ratio of total counterion charge to total polyelectrolyte charge, which causes formation of spherical aggregates. A desired photosensitive compound may then be added to the aggregates to form photosensitive polymer aggregates 2107. In an embodiment, a sol (suspension) of a predetermined type of nanoparticle 109 is then added to the same solution, whereupon these nanoparticles 109 arrange themselves around the photosensitive aggregates to form the outer shell 111. Generally, the aggregate cores may be spherical in geometry. The nanoparticles 109 infiltrate and/or encapsulate the aggregated photosensitive aggregate core 107. Further details of the microcapsules and methods of encapsulation may be found in U.S. patent application Ser. No. 10/969,391, filed Oct. 20, 2004, and U.S. patent application Ser. No. 11/335,328, filed Jan. 16, 2006 incorporated herein by reference in its entirety for all purposes.

The positively charged polyelectrolyte 101 may comprise a compound such as without limitation, polypeptides, polyamides, polyamines with different chain lengths with straight or branched structures (e.g., polylysine, polyallylamine, polyethyleneimine), or combinations thereof. In these embodiments, the counterion 103 is preferably negatively charged and comprises carboxylates, phosphates, sulfates, carbonates, aminocarboxylates, peptides, polypeptides, copolypeptides, polymers having negative charge (e.g. polyaspartic acid and polyglutamic acid), or combinations thereof. Alternatively, with a negatively charged polyelectrolyte 101, the counterion 103 is preferably positively charged and comprises cationic counterions such as polyamines. Examples of negatively charged polyelectrolyte 101 may include without limitation, polypeptides, polyacids polystyrenesulphonate, derivatives thereof, or combinations thereof. Suitable copolypeptides may be derived from the 20 natural amino acids or combinations thereof (e.g., lysine, arginine, histidine, aspartic acid, glutamic acid, glycine, alanine, valine, leucine, isoleucine, methionine, proline, phenylalanine, tryptophan, serine, threonine, asparagine, glutamine, tyrosine, and cysteine). Combinations of polypeptides and polymers may also be used.

The polyelectrolyte and the counterions are preferably selected and provided such that the overall charge ratio R of total charge attributable to the dissolved salt to total charge attributable to the polymer is greater than 1.0, alternatively greater than 3, alternatively greater than 5, and optionally about 10. When the polyelectrolyte is positively charged, R can be expressed as $R=[anion] \times |z-|/[polymer] \times |z+|$, where [anion] and [polymer] represent total concentrations, $z-$ is negative charge per anion, and $z+$ is positive charge per polymer chain. In embodiments in which the charges are reversed, the polyelectrolyte is negatively charged and the counterions are cations and $R=[cation] \times |z+|/[polymer] \times |z-|$.

The polyelectrolyte 101 is preferably dissolved in water, or in any other solvent that is capable of dissolving both the polyelectrolyte 101 and the counterion 103. The formation of the polymer aggregate core 105 can be carried out over a broad range of temperatures, limited primarily by the solvent. Thus, in some embodiments, the polyelectrolyte 101 and the counterion 103 are allowed to form at a temperature ranging from about 0° C. and about 100° C., alternatively from about 1° C. to about 50° C., alternatively from about 2° C. to about 20° C.

Any suitable photosensitive compound may be added to the aggregate cores 105 to form the photosensitive cores 107. Without being limited by theory, it is believed that the photosensitive compounds may bind or be coupled to the aggregate core 105 through surface charge interactions. Preferably, the photosensitive compound exhibits photosensitivity in the near-infrared (NIR) range (e.g. about 740 to about 3000 nm). Specifically, the photosensitive compound may have absorption wavelengths ranging from about 700 nm to about 1000 nm, preferably from about 720 nm to about 900 nm, more preferably from about 750 nm to about 850 nm.

In embodiments, the photosensitive compound may comprise water soluble fluorescent dyes. Examples of suitable photosensitive compounds include without limitation, indol-containing dyes, carbocyanine-containing dyes, polymethine dyes, azido-containing dyes, acridines, anthraquinones, benzimidazols, indolenines, napthalimides, oxazines, oxonols, polyenes, porphins, squaraines, styryls, thiazols, xanthins, other NIR dyes known to those of skill in the art, or combinations thereof. Alternatively, photosensitive compound may comprise photosensitive quantum dots. It is also contemplated that more than one type of photosensitive compound may be encapsulated by each microcapsule such that the photosensitive microcapsules may have different absorption wavelengths. For example, the photosensitive microcapsules may have absorption wavelengths at the NIR range and also the visible range (e.g. 400 nm-700 nm).

Figure 2:
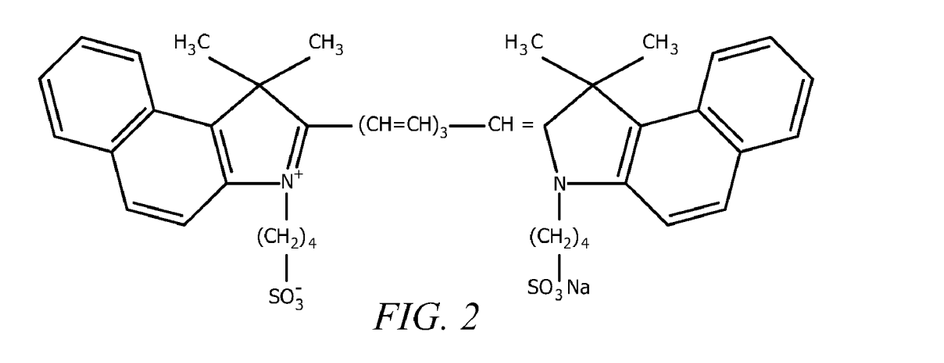
FIG. 2 illustrates the chemical structure of indocyanine green.

In an embodiment, the photosensitive compound is indocyanine green. Indocyanine green (ICG) is an amphiphilic carbocyanine dye (molecular weight=775.0, CAS No, =[3599-32-4]) that strongly absorbs and fluoresces in the near infrared region of light, exhibiting absorption and emission maxima at ~780 nm and ~820 nm, respectively. The chemical structure of ICG is shown in FIG. 2. With low toxicity (semilethal dose LD50 of 50-80 mg/kg for animal subjects and US Food and Drug Administration (FDA) approval for clinical use, ICG is used as a contrast agent to optically image the human vasculature for medical diagnostic applications (eg, retinal angiography since the 1970's). ICG has also been studied as a basis for medical treatment. It can convert the absorbed light energy to produce heat and chemical species (such as singlet oxygen, superoxide anions, and hydroxyl radicals), forming the respective bases for photothermal and photodynamic therapies.

The photosensitive compound may be encapsulated within the microcapsule at any suitable concentration. In embodiments where the polyelectrolyte is a polyamine, the concentration of photosensitive compound in each microcapsule may be quantified as a ratio of photosensitive compound to amines in the polymer aggregate. Accordingly, in such embodiments, the photosensitive compound may be encapsulated at photosensitive compound to amine ratios ranging from about 0.0001 to about 0.2, alternatively from about 0.02 to about 0.18, alternatively from about 0.03 to about 0.18. Additionally, the photosensitive compound may be encapsulated at concentration ranging from about 0.1 wt % to about 40 wt % of photosensitive compound, alternatively from about 0.4 wt % to about 23 wt %, alternatively from about 11 wt % to about 23 wt %.

As described above, the photosensitive polymer aggregate is surrounded by an outer shell or capsule. Preferably, the outer shell or capsule comprises nanoparticles. The nanoparticles can be silica or can comprise colloidal metals, such as gold, platinum, palladium, copper, silver, rhodium, rhenium, nickel, and iridium having surface positive/negative charge, alloys of metals, such as platinum/iridium having surface positive/negative charge, metal non-oxides, such as Group II-VI, III-V, and IV quantum dots having surface positive/negative charge, or metal oxides, such as titanium oxide, zirconium oxide, aluminum oxide, iron oxide, tungsten oxide, cerium oxide, antimony oxide and silicon oxide having surface positive/negative charge. In other embodiments, the nanoparticles may alternatively comprise molecular clusters, such as Keggin ions and heteropolymetallates, or may be organic and composed of crosslinked polymer, such as polystyrene and polypyrrole. Other examples of nanoparticles include without limitation, metal nanoparticles, metal oxide nanoparticles, metal-nonoxide nanoparticles, organic nanoparticles, polymeric nanoparticles, biomolecular nanoparticles, fullerenols, single/multi-walled carbon nanotubes, or combinations thereof.

In still other embodiments, the nanoparticles may be replaced with same-charged linear polymers, such as polyacrylate and polystyrene sulfonate, to form microcapsule structures via electrostatic interactions. The nanoparticles can also be provided in the form of uncharged polymers, such as dextran, to form microcapsule structures. Without being limited by theory, hydrogen-bonding and/or hydrophobic interactions rather than electrostatic interactions are believed to drive the adsorption of uncharged polymer into the polylysine-salt aggregates in these embodiments. Alternatively, the outer shell may comprise a solid polymeric outer shell rather than a nanoparticle shell. Thus, the outer shell may comprise polymeric or biological molecules such as Human Serum Album, dextran, polyethylene glycol, poly(acrylic acid, sodium salt), poly(sodium 4-styrenesulfonate), antibodies, or combinations thereof.

The formed photosensitive microcapsules have superior properties in comparison to other photosensitive compounds. Specifically, the photosensitive microcapsules display minimal leakage. In other words, over a period of time, embodiments of the photosensitive microcapsules will retain the encapsulated photosensitive compound for longer periods of time. More particularly, the photosensitive microcapsules are capable of retaining at least 97% of photosensitive compound after about 8 hours, alternatively at least about 85% of photosensitive compound after about 8 hours, alternatively at least about 50% of photosensitive compound after about 8 hours. Moreover, the photosensitive microcapsules are capable of retaining at least 100% of photosensitive compound after about 2 hours, alternatively at least about 90% of photosensitive compound after about 2 hours, alternatively at least about 85% of photosensitive compound after about 2 hours. In addition, the photosensitive microcapsules stabilize the encapsulated photosensitive compound allowing for increased number of irradiation cycles. For example, in some embodiments, the photosensitive microcapsules are capable of reaching a temperature of at least about 55° C. for at least 6 irradiation cycles, alternatively 8 irradiation cycles, alternatively 12 irradiation cycles.

The preparation of the photosensitive microcapsules may further include post-treatment of the particle surface with organic molecules, additional nanoparticles, and/or an inorganic coating. The microcapsules may further be functionalized with any suitable functional moiety for targeted or site-specific delivery of the photosensitive microcapsules. Examples of suitable functional moieties include without limitation, peptides, proteins, receptors, antibodies, ligands, amino acids, or combinations thereof.

The photosensitive microcapsules may be delivered or administered to a patient for phototherapeutic treatment. Any known methods of administration may be used. For example, the photosensitive microcapsules may be administered directly by a syringe into a treatment site such as a tumor. Alternatively, a catheter may be used to administer the photosensitive microcapsule intravenously. It is envisioned that the microcapsules that are administered systemically may be functionalized with binding moieties such that once administered the photosensitive microcapsules will preferentially bind to target tissues such as tumors, cancer cells, masses, or atherosclerotic plaque.

Once the photosensitive microcapsules have been administered to the patient, they may be irradiated with a light source 321 as shown in block 300 of FIG. 1. Preferably, the photosensitive microcapsules 113 are irradiated ex vivo where the microcapsules 113 are underneath a tissue surface 323 and the light source 321 is located outside a patient's body. However, the photosensitive microcapsules 113 may also be irradiated during a surgical procedure. In an embodiment, the photosensitive microcapsules 113 may be irradiated with a NIR laser. Other examples of suitable light sources 321 include without limitation laser diodes, semiconductor laser diodes, gas lasers, light emitting diodes (LEDs), or combinations thereof. The light source preferably emits light at a wavelength ranging from about 600 nm to about 3000 nm, alternatively from about 700 nm to about 1000 nm, alternatively from about 720 nm to about 850 nm.

In another embodiment, the photosensitive microcapsules may be administered as part of a drug delivery system. For example, the photosensitive microcapsules may be delivered within a matrix of polymeric material such as a thermoreversible hydrogel. The thermoreversible hydrogel, loaded with pharmaceutical compounds of any kind, may be deposited inside a patient and allowed to harden or gel. At the desired time, the thermoreversible gel may be irradiated with a light source to excite the photosensitive microcapsules, thereby heating the gel. The increase in temperature may cause the thermoreversible gels to swell and release the pharmaceutical compound into the body.

The photosensitive capsules may used in a variety of photothermal and photodynamic applications for diseases, such as without limitation, skin cancer or breast cancer. They can also be used in laser-welding and light-triggered drug-delivery system. The disclosed methods may also be considered as an alternative to gold nanoshells.

To further illustrate various illustrative embodiments of the present invention, the following examples are provided.

EXAMPLES

Methods and Materials

Materials

Poly(allylamine hydrochloride) ("PAH," 70 000 g/mol, chloride counterion, Sigma-Aldrich), disodium hydrogen phosphate heptahydrate ($Na_2HPO_4.7H_2O$, 99.5%, Fisher), and indocyanine green (ICG, ~90%, Sigma-Aldrich) were used as received. A nitric acid solution (70 wt % $HNO_3$, Fisher Science) was diluted to 2 wt %. Stock solutions of PAH, $Na_2HPO_4$, and ICG (1 mg/mL) were prepared using deionized water (18.2 MΩ, Barnstead Nanopure Diamond System) and stored at 4° C. before use. Silicon oxide NPs (13 nm diameter) were available as an aqueous colloidal suspension (20.5 wt %, pH 3.4, Snowtex-O, Nissan Chemicals) and used without further purification. Phosphate buffered saline (PBS) solution (0.01 M PO4 3-, 0.138 M NaCl, 0.0027 M KCl, pH 7.4) was prepared by using premade powder (Sigma-Aldrich).

Synthesis

Nanoparticle-assembled capsules (NACs) were synthesized by combining the PAH solution (2 mg/mL, 20 µL) with the $Na_2HPO_4$ solution (0.01 M, 120 µL) at room temperature. The ratio of total negative charge of the added salt to the total positive charge of the polymer, or the R ratio, was set at 6. The resulting suspension was aged for 10 min at 4° C., which was then combined and mixed with the $SiO_2$ sol (diluted to 7 wt %, 60 µL). The resulting NACs were aged for 2 h at 4° C. and washed twice with PBS solution.

IGC containing NACs (ICG-NACs) were prepared by adding the ICG solution (60 µL) of a given concentration (0 to 1.29 mM) to the 10 min aged polymer aggregate suspension and then adding the $SiO_2$ sol. These concentrations corresponded to precursor molar ratios of ICG to amine monomer units in the range of 0-0.18. The suspension was aged for 2 h at 4° C., and the capsules were recovered via centrifugation and washed twice with PBS. Unless stated otherwise, the capsules were resuspended in PBS solution. The synthesis of fluorescently labeled ICG-NACs was carried out by replacing PAH with PAH conjugated with FITC (fluorescein isothiocyanate), which was used for confocal microscopy.

Characterization

Fluorescence and bright-field optical microscopy images were obtained using a Leica DM2500 Research Microscope. Laser-scanning confocal microscopy was performed on a Carl Zeiss LSM 510 Meta microscope (laser excitations of 488 and 633 nm for FITC and ICG, respectively). The bandpass filter for FITC had a 500-550 nm range, and for ICG, 650-710 nm. Samples were mounted on conventional glass slides and sealed under a cover slip to prevent drying. All samples were prepared approximately 2-2.5 h prior to imaging, including NAC aging time. Line intensity profiles of ICG-NACs in fluorescence images were collected using ImageJ software. 45 Scanning electron microscopy (SEM) images were performed with FEI XL-30 environmental SEM operating at 30 kV with a working distance of 10.0 mm. The NACs were washed twice, loaded on a SEM stud, dried under air overnight, and sputter-coated with gold before SEM imaging. Absorbance spectra of ICG-containing solutions and ICG-NAC suspensions were performed using a UV-vis spectrometer (Shimadzu, model UV2401-PC). The samples were handled in a lowlight environment to minimize ICG interactions with ambient light. The hydrodynamic diameter of polymer aggregates was characterized through dynamic light scattering (Brookhaven, ZetaPALS with BI-9000AT digital autocorrelator, $\lambda=656$ nm). The electrophoretic mobility of these aggregates was measured by phase analysis light scattering (PALS) using the ZetaPALS setup. A dip-in (Uzgiris type) electrode system with 4 mL polystyrene cuvettes was used, and measurements were taken at 20° C.

ICG Loading Efficiency and Content Determination

The amount of ICG loaded into the NACs was determined from the free ICG that was not incorporated inside the NACs. Procedurally, one batch of ICG-NACs was centrifuged and the supernatant was carefully removed and stored in a 15 mL centrifuge tube; the capsules were dispersed in PBS solution. The centrifugation was repeated, and the collected supernatant was combined with the other supernatant volume. The ICG concentration was quantified via UV-vis spectroscopy. ICG decay was found to be negligible at the ICG concentrations measured, consistent with published reports of ICG stability at high concentrations in water. ICG inside the NACs were also measured to check the accuracy of the above method. Selected samples of ICG-NACs were treated with $HNO_3$ solution to induce capsule disassembly and ICG release into solution. For all samples tested, the amount of released ICG and unencapsulated ICG equaled the initial precursor ICG, indicating mass balance was closed. Loading efficiency was calculated as the mass of ICG incorporated by the NACs divided by the total ICG mass added to the polymer aggregate suspension. The loading content was calculated as the mass of ICG incorporated into the NACs divided by the mass of the dried ICG-NACs. Measurements were performed at least 3 times to ensure reproducibility.

ICG Leakage Measurements

The synthesis of ICG-NACs with ICG/PAH=0.04 was scaled up by 10 times. After washing with PBS solution, the precipitate was dispersed in PBS solution (2.6 mL) and split into 0.25 mL aliquots kept under constant shaking in the dark at either 23 or 37° C. Because of the long time scale of this study and the sensitivity of ICG to degradation in water, the suspension fluid was not analyzed for released ICG. Instead, the ICG contained within the ICG-NACs was quantified by inducing the disassembly of the ICG-NACs and immediately measuring the ICG concentration. Specifically, after a given aging time, each aliquot was centrifuged for 30 min and the concentrated precipitate suspension (500 µL) was combined with 2.5 mL HNO3 solution (2 wt %). The resulting clear solution was then analyzed through UV-vis spectroscopy. As control samples, fresh ICG solution in PBS was prepared with a concentration close to that of the disassembled NAC solution (~0.04 mg/mL) and incubated at 23 and 37° C. The samples were kept in the dark during aging.

Laser-Induced Photothermal Experiments

Washed ICG-NACs (0.5 mL, ~1×10$^7$ particles/mL, ~1×10$^9$ ICG molecules/particles, 0.007 wt % ICG of suspension) were suspended in PBS solution and placed in the wells of a 24 well polystyrene culture dish. Control samples were a 0.007 wt % PBS solution of ICG and PBS solution. Containing 0.5 mL of aqueous suspension or solution, each well was irradiated with a continuous-wave near-infrared diode laser (Coherent FAP-System, 54 W, $\lambda=808$ nm, irradiance ($I_o$)) 155 W/cm$^2$) for various time intervals. The laser beam impinged on the sample with a 6.66 mm diameter. During irradiation, the sample temperature was monitored with a K-type thermocouple (bead diameter) 0.003 in., Omega Engineering) located 1 mm outside the laser spot and recorded using LabVIEW data acquisition software (National Instruments, Austin, Tex.). For the SEM study, 5 identical batches were prepared and irradiated for various times. Each sample was then washed twice with Nanopure water and dried at room temperature for SEM imaging. Viability Assessment of Cells Exposed to ICG-NACs. Centrifuged ICG-NACs (20 µL, ~1×10$^8$ particles/mL, ~1×10$^9$ ICG molecules/particle, 0.02 wt % ICG of total suspension) were added to 24-well petri dishes containing cultured fibroblasts (rat maxillary incisor pulp cells (RPC-C2A), incubated in DMEM (Dulbecco's Modified Eagle's Medium) at 37° C. for 1 day; cell density of ~2000 cells/cm$^2$; 2 mL, growth area of 1.9 cm$^2$). Per well, the final concentration of ICG-NACs was ~0.0003 wt %, equivalent to final concentrations of 0.00004 wt % ICG, 0.00015 wt % PAH, and 0.00005 wt % $SiO_2$ NPs. The ICG-NAC/cell culture was incubated at 37° C. for 2 days; four wells were run in replicate. Cell survival was quantified using the Live/Dead viability assay (Molecular Probes). Dead cells were differentiated from live cells through fluorescence microscopy, as the former emitted red fluorescence (from the ethidium homodimer-1 dye precursor) and the latter emitted green fluorescence (from the calcein acetoxymethyl ester dye precursor). Other materials were similarly tested, at final concentrations higher than that of ICG-NACs: PAH solution (20 µL, 2 mg/mL, with a final concentration of 0.002 mg/mL or 0.002 wt %), SiO2 sol (20 µL, 0.2 wt %, pH 7, with a final concentration of 0.002 wt %), NAC suspension (20 µL, ~10$^7$ particles/mL, with a final concentration of ~0.0003 wt %), PBS solution of ICG (0.02 wt %, with a final concentration of 0.0002 wt %), and PBS solution.

Results

Figure 3:
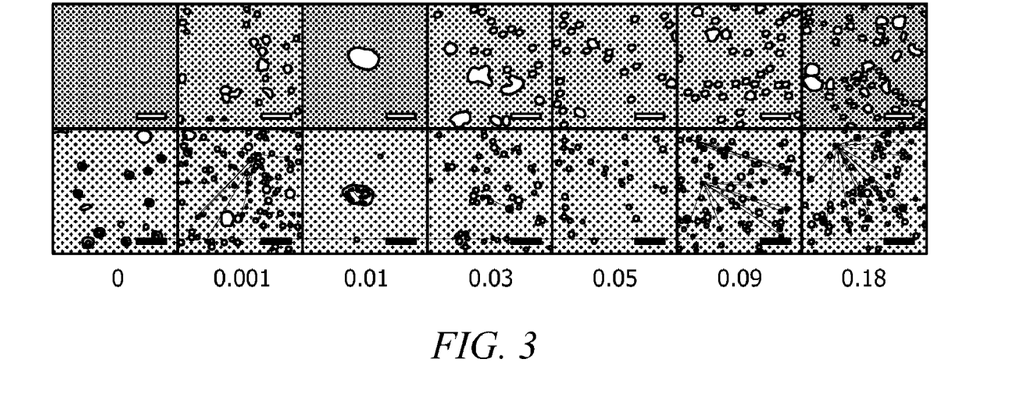
FIG. 3 illustrates fluorescence (top row) and bright-field (bottom row) optical images of photosensitive compound-containing polymer aggregates prepared with various photosensitive/amine precursor ratios (scale bar=10 μm)

The "encapsulation" of ICG within NACs entailed the addition of ICG molecules into the polymer aggregate intermediates before the $SiO_2$ NPs were added to form the shell (Encapsulated ICG will be seen to reside within the NAC shell and in the core interior). After the PAH/phosphate aggregate formation step, ICG was added to the suspension at various ICG/amine monomer precursor ratios. All suspensions were found with polymer aggregates containing ICG, according to fluorescence microscopy visualization (FIG. 3). The aggregates were spherical in shape and isolated from one another for most ICG/monomer ratios. There was an intermediate range in which the aggregates formed large clumps, as typified by the suspension prepared with ICG/amine ratio=0.01 (FIG. 3).

Figure 4:
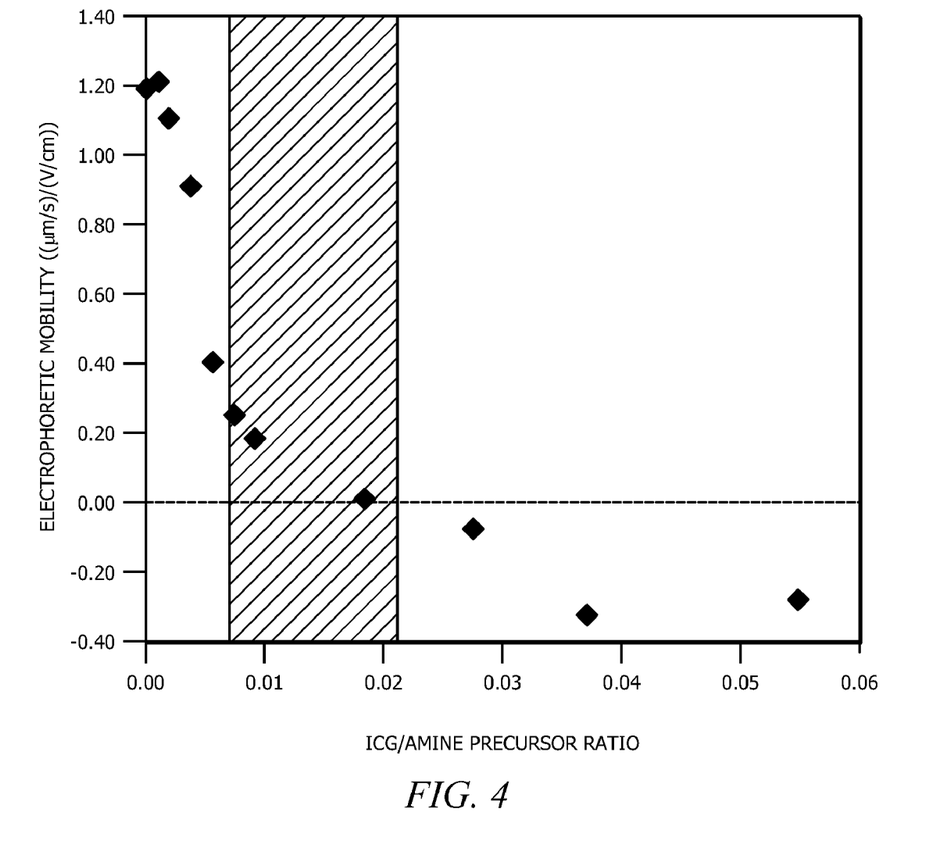
FIG. 4 shows electrophoretic mobility measurements of photosensitive compound-containing polymer aggregates prepared with variable amounts of photosensitive compound (e.g. ICG precursor)

Electrophoretic mobility ($\mu_E$) measurements were performed to gain insight into this clumping behavior. Without ICG, the PAH/phosphate aggregates were very positively charged, as indicated by the measured $\mu e$ value of +1.2 ($\mu m$/s)/(V/cm) (FIG. 4). The electrophoretic mobility decreased in magnitude with increasing ICG/PAH precursor ratio, eventually crossing over to negative values above ICG/amine=0.018. The polymer aggregates formed clumps in the ICG/amine range of 0.007 and 0.021, which could be correlated to near-zero $\mu_E$ values indicative of near-neutral net surface charge.

Figure 5:
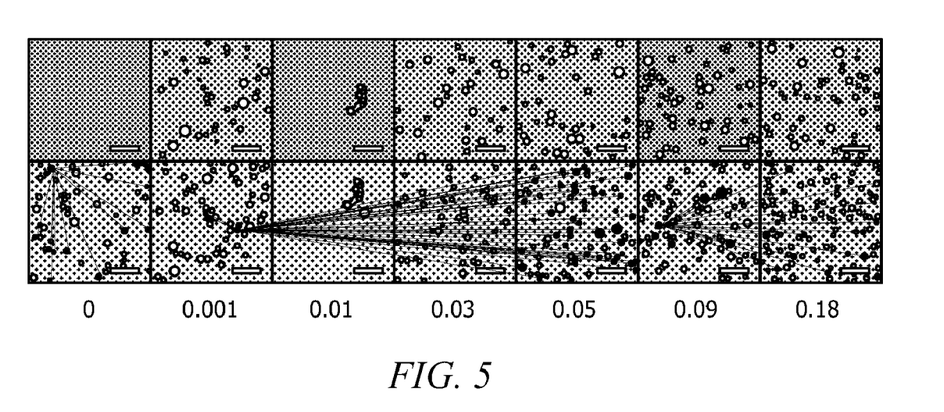
FIG. 5 shows fluorescence (top row) and bright-field (bottom row) optical images of photosensitive compound-containing microcapsules derived from the PAH/phosphate aggregates (prepared with various photosensitive compound/amine precursor ratios) shown in FIG. 3 (scale bar=10 μm)
Figure 6A:
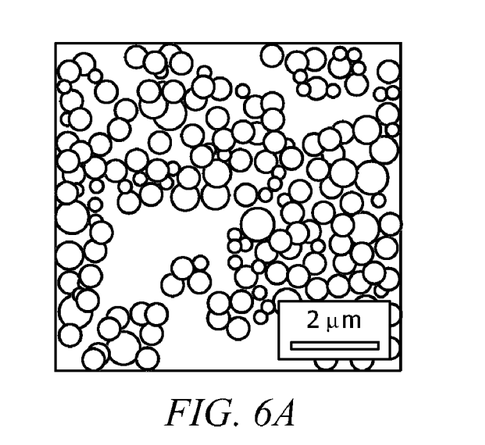
FIG. 6 shows (a) SEM image of dried photosensitive microcapsules, (b) fluorescence image of photosensitive microcapsules in aqueous suspension, and (c) fluorescence intensity line profile of one capsule as indicated in panel (b). The photosensitive microcapsules were prepared with an ICG/amine precursor ratio of 0.04.
Figure 8:
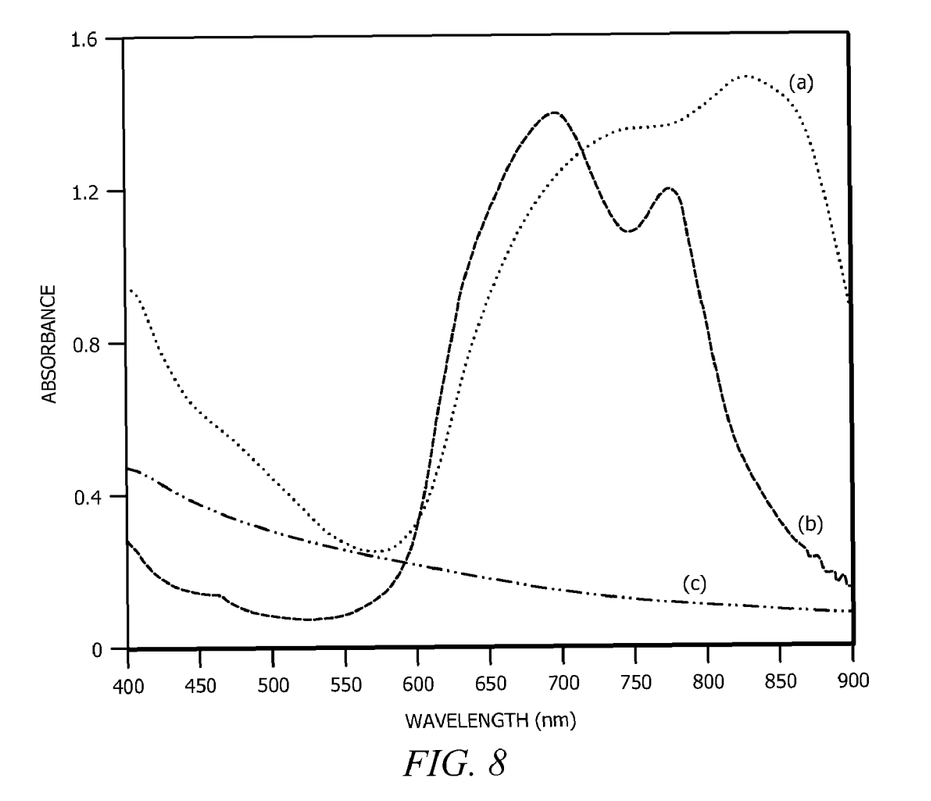
FIG. 8 shows UV-vis absorbance spectra of (a) photosensitive microcapsules, (b) PBS solution of ICG, and (c) non-photosensitive microcapsules.

The $SiO_2$ NP sol was added to the ICG-containing aggregate suspension form the ICG microcapsules (FIG. 1). The resulting ICG-NACs assumed the shape and disperse state of the parent aggregates. The sample prepared with an ICG/amine ratio of 0.01 contained ill-defined particles due to the clumping of the polymer aggregates. As in the case of the parent aggregates, there was no apparent trend in capsule size with ICG precursor amount (FIG. 5). All the ICG-NACs were roughly 1 $\mu m$ in diameter, with the largest ones observed with a diameter of 2 $\mu m$, and the smallest, 0.6 $\mu m$. Dried under vacuum during SEM imaging, the ICG-NACs underwent contraction like the NACs prepared using poly(lysine) instead of PAH, resulting in capsules with diameters less than 1 $\mu m$ (FIG. 6a). They did not fracture or deform after drying, maintaining their spherical shape. In suspension, the ICG-NACs were colloidally stable and did not precipitate even after 6 months. Macroscopically, they appeared as a greenish and cloudy suspension, which could be readily centrifuged to give a green-colored precipitate and a colorless supernatant (FIG. 7).

from the suspended NAC particles contributed to a higher background in the absorbance spectrum, as was seen for the case of the non-ICG-containing NAC suspension (FIG. 8c). In contrast, an aqueous ICG solution of the same ICG concentration had peaks located at 780 nm and 700 nm, representing ICG monomers (single ICG molecules) and dimers (aggregates of 2 ICG molecules), respectively (FIG. 8b).

Figure 6B:
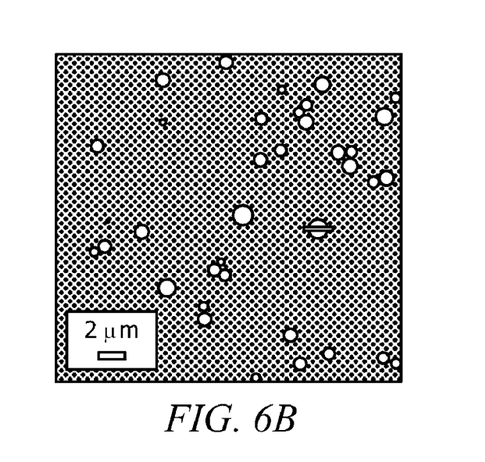
Figure 6C:
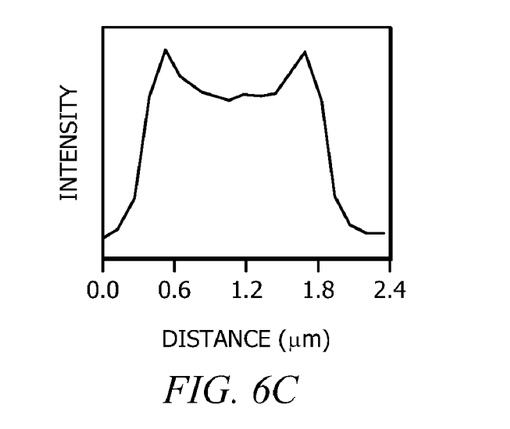
Figure 7A:
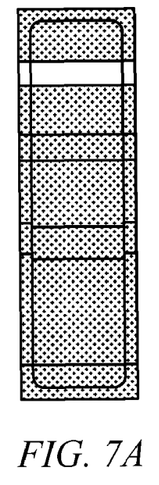
FIG. 7 shows cuvettes containing photosensitive capsules (a) before and (b) after centrifugation; (c) PBS solution of ICG; and (d) non-photosensitive microcapsules. The double-lines are drawn in the background to aid in observing suspension cloudiness.
Figure 7B:
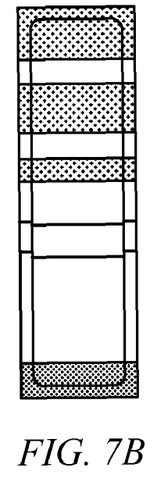
Figure 7C:
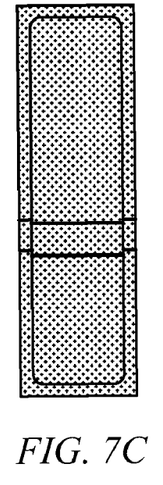
Figure 7D:
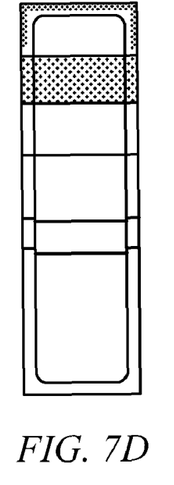
Figure 13A:
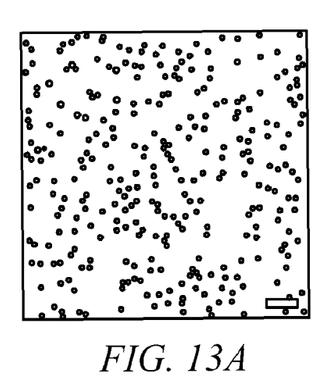
FIG. 13 shows (a) brightfield and confocal images of photosensitive microcapsules prepared with PAH-FITC for (b) FITC and (c) ICG.
Figure 13B:
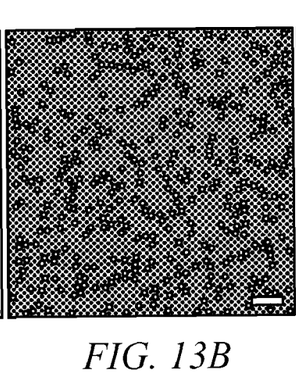
Figure 13C:
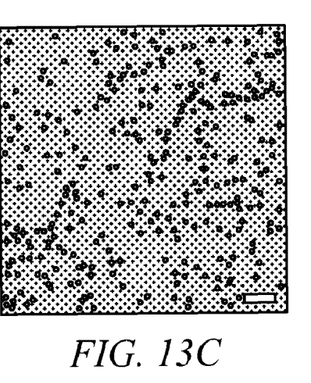

ICG molecules appeared to be more concentrated in the periphery of both the polymer aggregate intermediates and the resultant NACs (FIGS. 3, 5, and 6b). Upon closer examination, ICG-NACs were found to fluoresce within the core interior also (FIG. 6c). These data indicated that ICG was encapsulated in the hollow of the NACs and within the shell wall. Confocal analysis of ICG-NACs synthesized with PAH-FITC verified that the capsules were polymer-filled, that is, the PAH filled the hollow of the capsule (FIG. 13). Thus, ICG was distributed throughout the NAC volume through electrostatic and hydrophobic interactions within the hollow and the shell.

Release of ICG from ICG-Containing NACs

Figure 9:
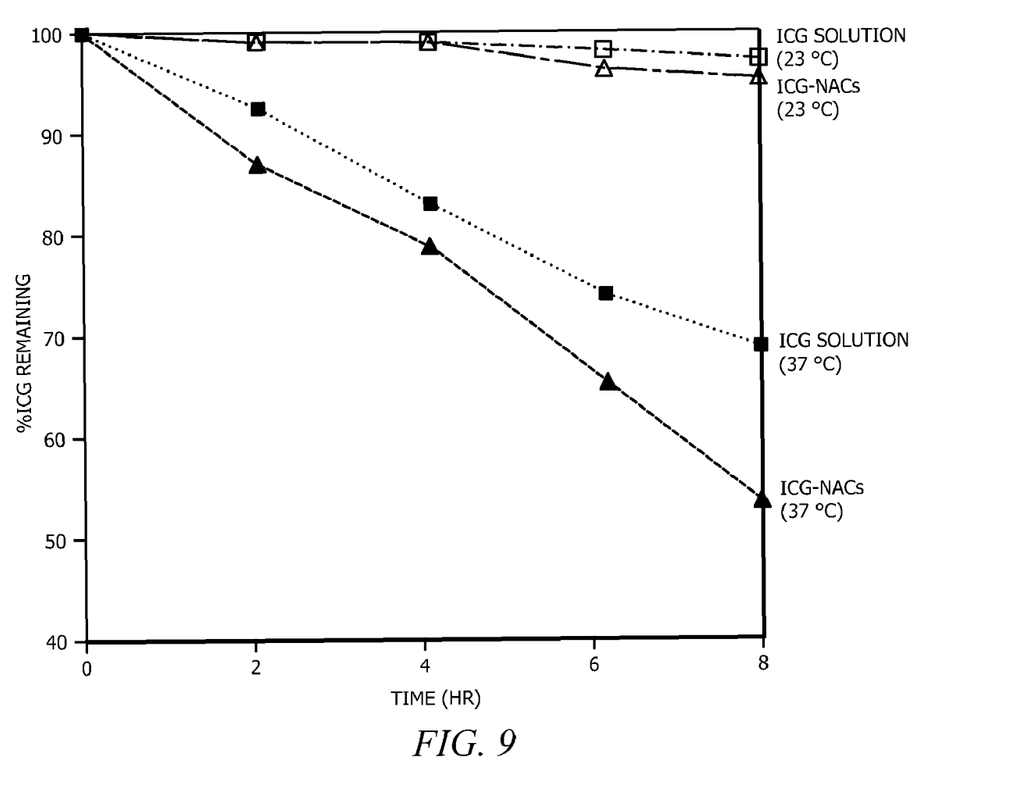
FIG. 9 shows ICG amount remaining in photosensitive microcapsules and free ICG solution as a function of time, at two different temperatures (23 and 37° C.)
Figure 14A:
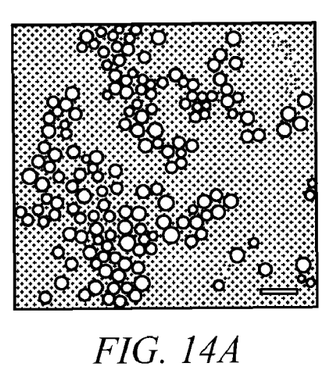
FIG. 14 shows (a) fluorescence and (b) brightfield images of photosensitive microcapsules (scale bar=2 μm).
Figure 14B:
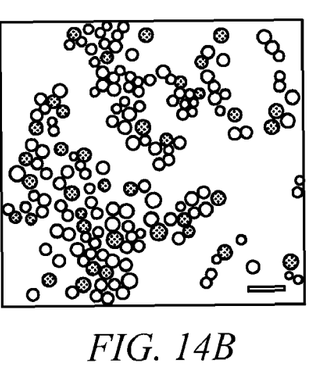

The ICG content of ICG-NACs (ICG/amine ratio=0.04) was quantified as a function of time by dis-assembling the capsules and measuring the absorbance of free ICG concentration at 780 nm (FIG. 9). For ICG-NACs at 23° C., more than 96% of ICG was retained. The small loss of ICG was partially the result of thermal degradation, as indicated by the small but finite concentration decrease of the ICG solution. At 37° C., thermal degradation of free ICG was significant, as ~35% was lost at the end of 8 hr. The half-life of ICG at 37° C. was calculated to be 19 hr, consistent with the published half-life of ~10 hr for an ICG concentration of 0.001 mg/ml at 42° C. In encapsulated form, ~50% of the ICG was lost at the end of 8 hr. Accounting for the ICG loss due to thermal degradation, we attributed the difference of 17% to ICG leakage from the capsule. The capsules were not broken (FIG. 14), suggesting the leakage was through diffusional loss instead of capsule rupture.

The ICG-NACs were compared with the ICG-containing PLGA particles. As mentioned earlier, the PLGA particles did not contain much ICG (with a reported maximum loading of 0.3 wt %) relative to ICG-NACs (Table I), and ICG leakage was significant. Specifically, 78% of ICG was lost from the

TABLE 1

| | ICG/amine ratio | | | | | | |
|---|---|---|---|---|---|---|---|
| | 0.001 | 0.03 | 0.04 | 0.05 | 0.07 | 0.09 | 0.18 |
| Loading efficiency (%) | 91.4 ± 4.4 | 97.1 ± 3.8 | 95.2 ± 3.4 | 90.0 ± 2.7 | 80.6 ± 2.9 | 65.5 ± 3.2 | 34.1 ± 2.9 |
| Loading content (wt %) | 0.4 ± 0.02 | 11.3 ± 0.4 | 14.3 ± 0.5 | 19.2 ± 0.6 | 22.1 ± 0.8 | 22.4 ± 1.1 | 23.1 ± 2.0 |

The NACs had loading contents ranging from 0.4 to 23.1 wt % (Table 1). The loading content could be increased by using higher ICG/amine ratios, but the loading efficiency correspondingly decreased (from as high as 97% to as low as 34%). The ICG/PAH ratios between 0.03 and 0.05 were observed to have high loading efficiency and loading content. For comparison, prior art ICG-containing PLGA particles had loading efficiencies of only 75% and loading contents of only 0.3 wt %.

Absorbance Properties of ICG-Containing NACs

The absorbance of ICG-NACs were analyzed by considering NACs prepared with ICG/amine ratio=0.04. ICG-NACs clearly exhibited absorption in the NIR and partially in the visible range, with an absorbance peak located at 830 nm and a less intense shoulder at 740 nm (FIG. 8a). Light scattering PLGA particles over an 8-hr period at 37° C. in PBS, leaving behind ~0.07 wt % ICG. Under the same conditions, the ICG-NACs prepared with ICG/amine ratio=0.04 retained ~7.2 wt % ICG (FIG. 9). ICG loss due to thermal degradation and leakage (<15% at 2 hr) is acceptable on the short time scales of photothermal therapies (~1-2 hrs).

Photothermal Behavior of ICG-Containing NACs

Figure 10A:
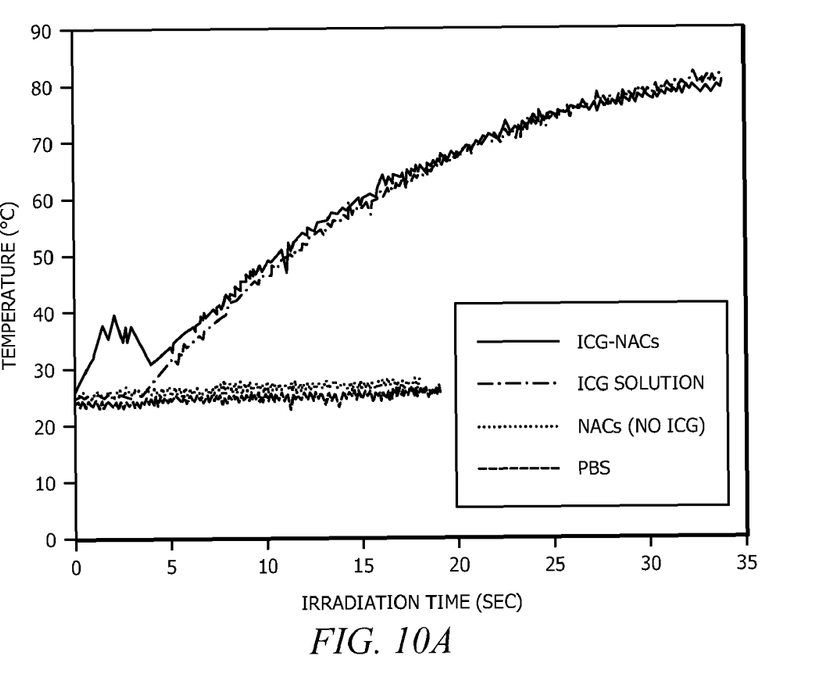
FIG. 10 shows temperature profiles of photosensitive microcapsules: (a) constant irradiation to 80° C., and (b) multiple-cycle irradiation/cooling.

The ICG-NACs were capable of laser-induced heat generation, with temperatures reaching >80° C. after ~30 sec of laser irradiation (FIG. 10a). An ICG solution of comparable concentration had a very similar heating curve, which indicated that entrapment of ICG within the NAC structure did not affect its photothermal response. Neither the buffer solution nor the non-ICG-containing NACs contributed to the observed temperature increase. The temperature spikes and heating delay during the first 5 seconds were experimental artifacts.

These experiments raised the question of NAC thermal stability during irradiation. We analyzed the capsules after various irradiation times through SEM (FIG. 11), finding that the ICG-NAC structure was mostly unaffected at 50° C. and lower. They were still spherical but the shell appeared to have some surface restructuring. At 60° C. and higher, the capsules experienced significant structural deformation. 50° C. appeared to be the transition temperature for the thermal stability of ICG-NACs.

Figure 10B:
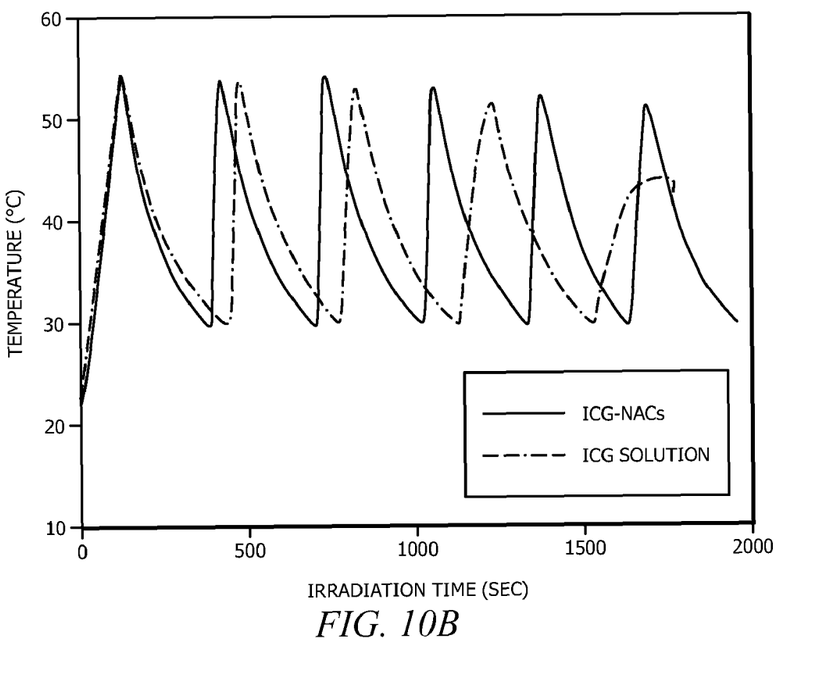
Figure 11A:
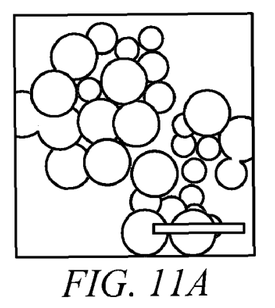
FIG. 11 shows SEM images of photosensitive microcapsules irradiated to different temperatures, under conditions used in FIG. 10a: (a) 23, (b) 40, (c) 50, (d) 60, (e) 70, and (f) 73° C. (scale bar=2 μm)
Figure 11B:
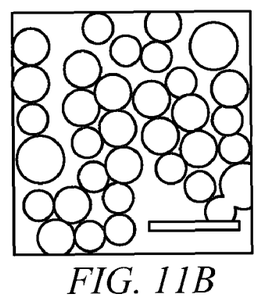
Figure 11C:
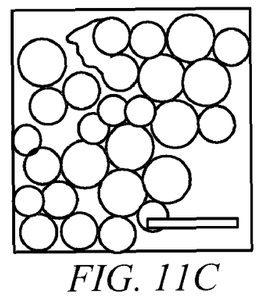
Figure 11D:
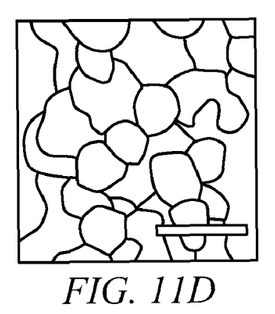
Figure 11E:
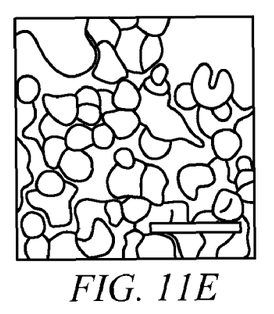
Figure 11F:
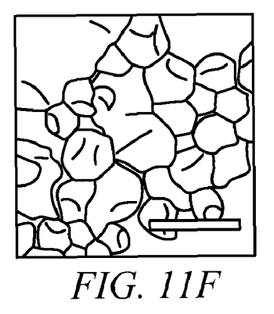

A further comparison of the ICG-NACs and free ICG was made by performing several cycles of photothermal heating and cooling (FIG. 10b). Each sample was irradiated until their temperature reached temperatures in the range of ~51-54° C., after which each was allowed to cool to 30° C. before repeating the irradiation. The photothermal heating patterns were found to be quite different. The ICG solution underwent 4 irradiation/cooling cycles before the 51° C. temperature clearly became unreachable, as a result of photodegradation of the ICG molecules. Photodegradation leading to ICG loss may be from the high temperatures generated or to direct photo-induced decomposition. On the fourth cycle, the temperature increase was noticeably less steep than the earlier cycles and a longer irradiation time was needed to reach 52° C., indicating ICG degradation became significant. In contrast, ICG-NACs were able to reach 55° C. for at least 6 cycles, with little change in the heating profiles. Thus, NAC encapsulation increases the stability of ICG against photodegradation.

Viability of Cells Exposed of ICG-Containing NACs

Figure 12:
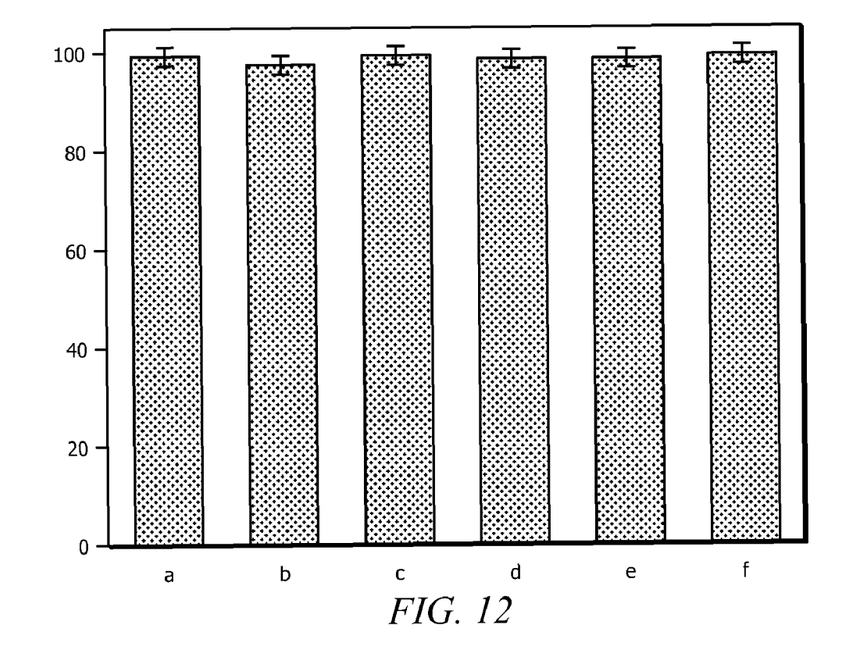
FIG. 12 shows results of viability testing of microcapsule precursors (a) PAH solution, (b) SiO2 nanoparticle sol, (c) PBS solution of ICG and capsules (d) non-photosensitive microcapsules, (e) photosensitive microcapsules, (f) PBS solution is a control sample.

The biocompatibility of the ICG-NACs was studied by incubating the microcapsules with fibroblast cells at 37° C. for 2 days. The ICG-NACs were found to be non-toxic, as were the PAH polymer, silica NPs, ICG, and non-ICG-containing NACs (FIG. 12). Recalling that the silica NPs are amorphous, these results are consistent with other studies that indicate amorphous silica powders and nanoparticles are non-toxic, especially compared to crystalline silica.

In summary, stable aqueous suspensions of ICG-containing hollow spheres were synthesized easily through a 3-step mixing process at room temperature and in water. At a loading as high as 23 wt % of the total material, the ICG molecules were located within the NP/polymer shell wall and within the polymer aggregate core. Absorbance spectra of ICG-NACs demonstrated that the peak absorption was red-shifted from that of free ICG by ~50 nm. At the physiological temperature of 37° C., ICG loss from the capsule was due to intrinsic thermal instability of the dye and to leakage. The ICG-containing capsules were active for NIR laser-induced heating, and were more photostable than free ICG. Restructuring of the shells was induced by photothermal heating above 50° C. The ICG-NACs offer the advantages of high ICG content, minimal leakage compared to other ICG-containing particles, and a functionalizable surface, which would be highly useful for targeted photothermal therapy.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference in the Description of the Related Art is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A method of encapsulating a photosensitive compound comprising:
   a) providing an amount of a polyelectrolyte having a charge and an amount of a counterion having a valence of at least 2;
   b) combining the polyelectrolyte and the counterion in a solution such that the polyelectrolyte self-assembles to form one or more aggregate cores;
   c) adding the one or more photosensitive compounds to the aggregate cores to form one or more photosensitive aggregate cores; and
   d) adding a coating material to the photosensitive aggregate cores such that the coating material arranges itself around the photosensitive aggregate cores to form a shell and encapsulate the photosensitive compound.

2. The method of claim 1 wherein the photosensitive compound has a negative charge.

3. The method of claim 1 wherein the photosensitive compound is indocyanine green.

4. The method of claim 1 wherein the polyelectrolyte is a polyamine and the counterion is a phosphate.

5. The method of claim 1 wherein (c) comprises adding the one or more photosensitive compound at a photosensitive compound to amine ratio ranging from about 0.001 to about 0.18.

6. The method of claim 1 wherein the charge ratio R of total charge of the counterions to the total charge of the polyelectrolyte is about 6.

7. The method of claim 1, wherein the photosensitive compound is present in an amount of greater than about 20 wt. %.

* * * * *